United States Patent [19]

Coppell et al.

[11] 4,073,807
[45] Feb. 14, 1978

[54] PROPIONAMIDE ANTITUMOR AGENTS

[75] Inventors: Stephen M. Coppell, Chinnor; Terence A. Harrow, High Wycombe, both of England

[73] Assignee: G. D. Searle & Co., Chicago, Ill.

[21] Appl. No.: 760,871

[22] Filed: Jan. 21, 1977

[30] Foreign Application Priority Data

Jan. 23, 1976 United Kingdom ............. 2654/76

[51] Int. Cl.² .................. C07C 103/44; A61K 31/16
[52] U.S. Cl. ............................ 260/562 N; 424/324
[58] Field of Search ................. 260/562 N; 424/324

[56] References Cited

U.S. PATENT DOCUMENTS 2,876,262  3/1959  Ehrhart et al. ............... 260/562 N
3,542,850  11/1970  Jansen et al. ............. 260/562 N X

OTHER PUBLICATIONS

Bergel et al., CA 55:2505e (1961).
Safonova et al., CA 60:15978h (1964).
Safonova et al., CA 55:7325i (1961).

Primary Examiner—Daniel E. Wyman
Assistant Examiner—Thomas A. Waltz
Attorney, Agent, or Firm—John J. McDonnell

[57] ABSTRACT

The present invention encompasses compounds of the formula

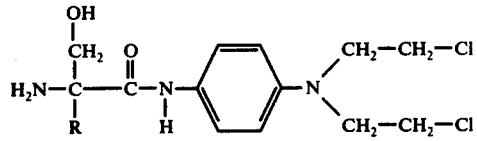

and the pharmaceutically acceptable acid addition salts thereof wherein R represents hydrogen or hydroxymethyl. The compounds of the present invention are prepared by condensing N-carbobenzyloxyserine or 2-carbobenzyloxyamino-3-hydroxy-2-hydroxymethylpropionic acid with p-[N,N-bis(2-chloroethyl)]-phenylenediamine hydrochloride and removing the carbobenzyloxy protecting group by catalytic hydrogenation. These compounds are useful as cytotoxic agents, in particular, antitumor agents.

3 Claims, No Drawings

PROPIONAMIDE ANTITUMOR AGENTS
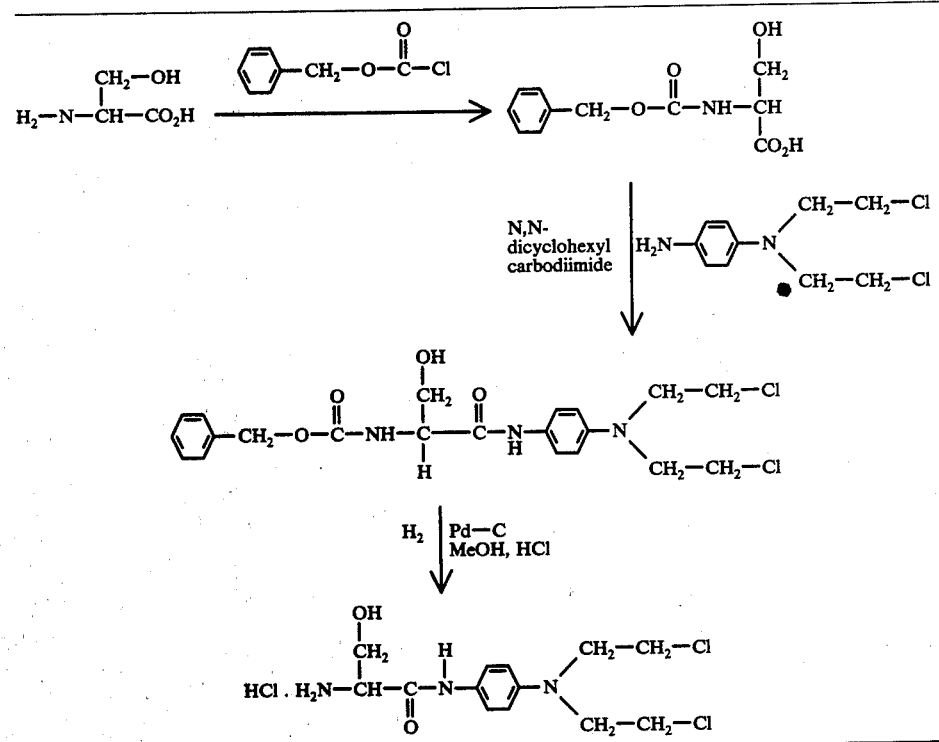
Compounds of the present invention are prepared according to the reaction Schemes A and B as follows:
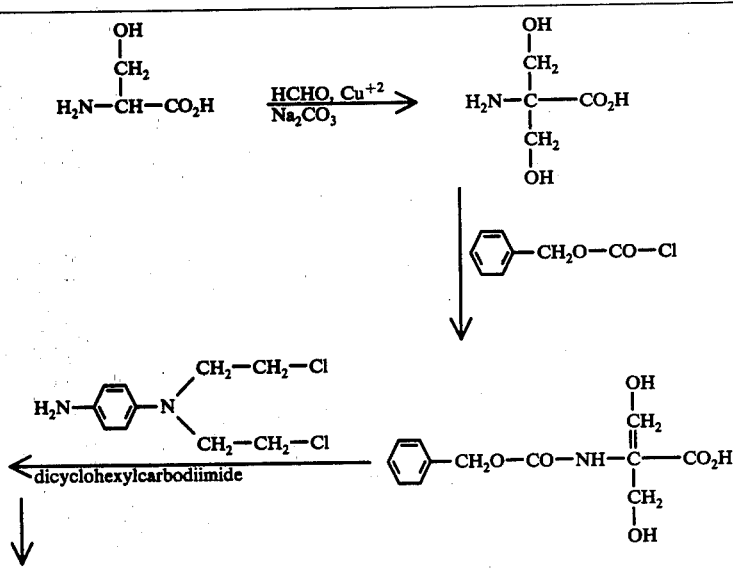

EXAMPLE 1

2.39 Parts of N-carbobenzyloxy-L-serine and 2.69 parts of p-[N,N-bis(2-chloroethyl)]phenylenediamine hydroxhloride were stirred together at room temperature and in the dark as a suspension in 50 parts by volume of dry methylene chloride. Then 1.01 parts of distilled triethylamine was added and stirring was continued for 30 minutes. A solution of 2.16 parts of N,N-dicycohexylcarbodiimide in 50 parts by volume of dry methylene was added over 10 minutes. Stirring was continued for 24 hours to provide a dark solution and a white precipitate. The reaction mixture was filtered and the filtrate was successively washed with aqueous sodium bicarbobate, 2 molar hydrochloric acid, and water. The organic layer was then dried over sodium sulfate and filtered and removal of solvent in vacuo provided a crude solid which after recrystallization from acetone/hexane or toluene provided 2-carbobenzyloxyamino-N-[p-bis(2-chloroethyl)amino]phenyl-3-hydroxypropionamide, melting at 145°–146° and having the following structural formula

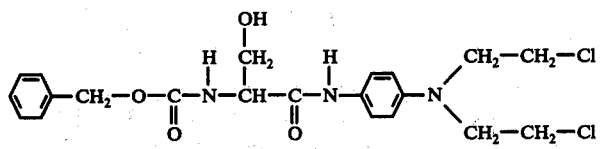

0.85 Parts of this material was dissolved in 85 parts by volume of distilled methanol containing 0.2 parts by volume of concentrated lhdrochloric acid and the solution hydrogenated at room temperature and atmospheric pressure over 0.17 parts of a 5% palladium-on-charcoal calalyst. The catalyst was removed by filtration, the solvent removed in vacuo, and the product was precipitated upon addition of dry ether. 2-Amino-N-[p-bis(2-chloroethyl)-amino]phenyl-3-hydroxypropionamide hydrochloride is isolated as a hydroscopic solid having the formula

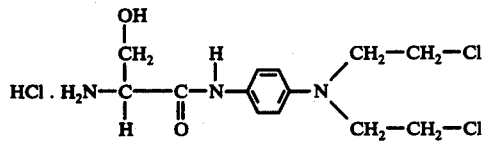

Replacement hydrochloric acid with an equivalent amount of sulfuric, phosphoric, hydrobromic, hydriodic, sulfamic, citric, lactic, maleic, malic, russinic, tartaric, cinnamic, acetic, benzoic, gluconic, ascorbic acid provide the corresponding acid addition salt. Neutralization of the acid salt with base and extraction with ether provides the free base, 2-amino-N-[p-bis(2-chloroethyl)amino]phenyl-3-hydroxypropionamide.

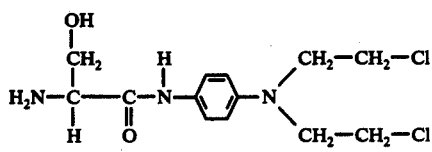

EXAMPLE 2

5.9 Parts of DL-serine was dissolved in 1100 parts by volume of 0.2 molar sodium carbonate. 5.6 parts by volume of a 1.0 molar cupric sulfate solution was then added, followed by 34 parts by volume of 40% aqueous formaldehyde solution. The solution was then heated at 95°–100° C for 20 minutes and a precipitate of copper resulted.

The reaction mixture was allowed to cool to room temperature and then filtered to remove the precipitated copper. After acidification with glacial acetic acid, the solution was concentrated under reduced pressure to around 100 parts by volume and then poured onto a Zeolite 225 ion exchange column, H form. This was washed with water until the acid band disappeared, when the column was eluted with 2M ammonium hydroxide, collecting and combining those fractions which gave a positive ninhydrin reaction. These fractions were then concentrated in vacuo, when IMS (95% ethanol) was added to precipitate the required product. After standing at 0° C for 3 days the crude product was filtered off, washed with IMS, and then recrystalized from IMS/water to afford 2-amino-3-hydroxy-2-hydroxymethylpropionic acid, melting at 253°–254° C and having the following structural formula

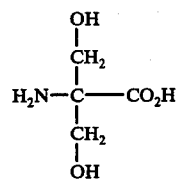

19.20 parts of this propionic acid is reacted with 21.56 parts of volume of N-benzylchloroformate in 236 parts by volume of N-benzylchloroformate in 236 parts by volume of sodium bicarbonate containing 29.8 parts of sodium carbonate. Following the procedure set out in Example 1, 2-carbobenzyloxyamino-3-hydroxy-2-hydroxymethylpropionic acid, melting at 109°–112° C (lit 112°–114°) is isolated. This compound has the following structural formula

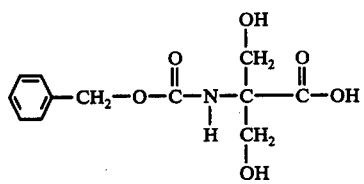

1.0 parts of this material were placed with 1.1 parts of p-[N,N-bis(2-chloroethyl)]phenylenediamine hydrochloride in 20 parts by volume of methylene chloride. 0.418 Parts of distilled triethylamine was added with continuing stirring and after stirring for 10 minutes 0.85 parts of N,N-dicyclohexylcarbodiimide in 20 parts by volume of dry methylene chloride was added over a 10 minute period. The reaction was worked up as in Example 1 to provide 2-carbobenzyloxyamino-N-[p-bis(2-chloroethyl)amino]phenyl-3-hydroxy-2-hydroxymethylpropionamide, melting at 138°–141° C, and having the following structural formula

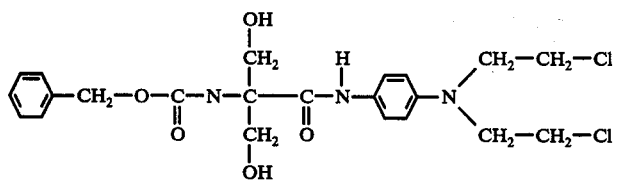

Using equivalent quantities and following the procedures in Example 1, 0.5 parts of this material is catalytically hydrogenated over 5% palladium-on-charcoal catalyst to provide 2-amino-N-[p-bis(2-chloroethyl)amino]-phenyl-3-hydroxy-2-hydroxymethylpropionamide hydrochloride having the following structural formula

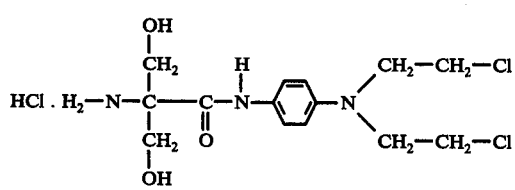

Other pharmaceutically acceptable acid addition salts and the free base 2-amino-N-[p-bis(2-chloroethyl)-amino]phenyl-3-hydroxy-2-hydroxymethylpropionamide are prepared as described in Example 1.

Alternatively, 5.20 parts of 2-carbobenzyloxyamino-3-hydroxy-2-hydroxymethylpropionic acid and 5.95 parts of 1-hydroxy benzotriazole in 130 parts by volume of dry methylene chloride are reacted. To this reaction mixture was added 4.03 parts of N,N-dicyclohexylcarbodimide and stirring continued for 16 hours. Then 5.7 parts of p-[N,N-bis(2-chloroethyl)]phenylenediamine hydrochloride and 2.99 parts by volume of triethylamine are added and stirred for 65 hours and worked up as earlier described to provide 2-carbobenzyloxyamino-N-[p-bis (2-chloroethyl)-amino]-phenyl-3-hydroxymethylpropionamide.

What is claimed is:

1. A compound of the formula

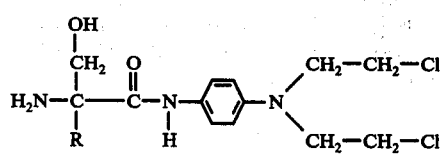

wherein R is hydrogen or hydroxymethyl.

2. A compound according to claim 1 which is 2-amino-N-[p-bis(2-chloroethyl)amino]-phenyl-3-hydroxypropionamide.

3. A compound according to claim 1 which is 2-amino-N-[p-bis(2-chloroethyl)amino]-phenyl-3-hydroxy-2-hydroxymethylpropionamide.

* * * * *